(12) United States Patent  (10) Patent No.: US 9,327,039 B2
Greenwood et al.  (45) Date of Patent: *May 3, 2016

(54) PARTICLE SIZE REDUCTION APPARATUS, AND USE THEREOF

(75) Inventors: Alan K. Greenwood, Hitchin (GB); Derek McHattie, Stotfold (GB); Parveen Bhatarah, Middlesex (GB); Gary Hembra, Arlesey (GB)

(73) Assignee: Resolution Chemicals Limited, Stevenage, Hertfordshire (GB)

( * ) Notice: Subject to any disclaimer, the term of this patent is extended or adjusted under 35 U.S.C. 154(b) by 551 days.

This patent is subject to a terminal disclaimer.

(21) Appl. No.: 12/648,122

(22) Filed: Dec. 28, 2009

(65) Prior Publication Data

US 2010/0099653 A1  Apr. 22, 2010

Related U.S. Application Data

(62) Division of application No. 11/118,765, filed on May 2, 2005, now Pat. No. 7,644,880.

(30) Foreign Application Priority Data

Dec. 16, 2004  (GB) .................................. 0427568.1

(51) Int. Cl.
  *A61K 9/14*  (2006.01)
  *A61L 2/07*  (2006.01)
  *A61L 2/04*  (2006.01)

(52) U.S. Cl.
  CPC ... *A61L 2/07* (2013.01); *A61L 2/04* (2013.01); *A61K 9/14* (2013.01)

(58) Field of Classification Search
  CPC .............. A61J 1/06; A61K 8/044; A61K 8/63
  See application file for complete search history.

(56) References Cited

U.S. PATENT DOCUMENTS

| | | | |
|---|---|---|---|
| 3,545,683 A | 12/1970 | Schulte | |
| 3,667,688 A | 6/1972 | Iannicelli | |
| 5,810,267 A | 9/1998 | Karasawa | |
| 5,904,932 A * | 5/1999 | De Vringer | 424/450 |
| 5,976,574 A * | 11/1999 | Gordon | 424/489 |
| 5,993,781 A * | 11/1999 | Snell et al. | 424/45 |
| 6,187,765 B1 | 2/2001 | Harris et al. | |
| 6,464,958 B1 | 10/2002 | Bernini et al. | |
| 6,491,897 B1 * | 12/2002 | Freund et al. | 424/45 |
| 6,680,110 B1 | 1/2004 | Deeb et al. | |
| 7,644,880 B2 | 1/2010 | Greenwood et al. | |
| 2002/0071870 A1 | 6/2002 | Sharma | |
| 2002/0103212 A1 | 8/2002 | Serizawa et al. | |

(Continued)

FOREIGN PATENT DOCUMENTS

DE  10145361 A1 *  4/2003
EP  0601724  6/1994

(Continued)

OTHER PUBLICATIONS

Pilot Scale Microfluidizer Processors—Models A, B and C, Microfluidics, United States (2003).

*Primary Examiner* — Benjamin Packard
(74) *Attorney, Agent, or Firm* — Florek & Endres PLLC

(57) ABSTRACT

A sterilizable particle-size reduction apparatus, component parts thereof and a method of sterilizing and validating sterility thereof are provided. Also provided is use thereof to prepare sterile suspensions of drugs.

15 Claims, 5 Drawing Sheets

(56) References Cited

U.S. PATENT DOCUMENTS

| | | | |
|---|---|---|---|
| 2002/0134373 A1* | 9/2002 | Gonda | 128/200.14 |
| 2003/0091513 A1* | 5/2003 | Mohsen et al. | 424/46 |
| 2005/0208083 A1 | 9/2005 | Annis | |
| 2005/0222108 A1 | 10/2005 | Bhatarah et al. | |

FOREIGN PATENT DOCUMENTS

| | | |
|---|---|---|
| GB | 285258 | 2/1928 |
| GB | 1049685 | 11/1966 |
| GB | 2275876 | 9/1994 |
| JP | 11-42428 | 2/1999 |
| JP | 2000-325031 | 11/2000 |
| JP | 2004-174481 | 6/2004 |
| RU | 2080165 | 5/1997 |
| WO | 92/08719 | 6/1992 |
| WO | 92/09368 | 6/1992 |
| WO | 94/08719 | 4/1994 |
| WO | 99/07466 | 2/1999 |
| WO | 99/25359 | 5/1999 |
| WO | 00/25745 | 5/2000 |
| WO | 00/25746 | 5/2000 |
| WO | 03/070285 | 8/2003 |
| WO | 2004/087204 | 10/2004 |
| WO | 2005/018687 | 3/2005 |

* cited by examiner

PARTICLE SIZE REDUCTION APPARATUS, AND USE THEREOF

BACKGROUND OF THE INVENTION

1. Field of the Invention

This invention relates to a particle-size reduction apparatus, sterilisation thereof and use thereof to prepare suspensions of drugs, in particular for administration via nebulizers.

2. Description of the Related Art

Previously it was acceptable for drugs intended for use in nebulizers to be prepared under "clean" conditions. Recently, however, such formulations have caused problems in the US due to contamination, and the US FDA has implemented a requirement for all nebulizer solutions to be sterile. In the light of the US FDA decision it is necessary to produce sterile suspension drugs in the US.

The sterilisation of suspensions raises particular problems. The standard means of sterilisation—that is, the raising of the temperature of the formulation to 121° C. for 15 minutes—frequently destroys one or more of the components of the formulation, so only chemically thermostable products can be sterilised by this method. The desired biological activity of the formulation commonly requires that the mass median diameter of particles of the drug lie within a narrow range (average diameter typically less than 5 μm). End sterilisation may alter particle size. In addition this treatment results in the clumping or agglomeration of the drug particles in the suspension such that the efficacy of the resulting product is impaired or abolished.

Known alternative methods for the sterilisation of pharmaceuticals are inappropriate for sterilising suspension formulations of drugs. Solutions of pharmaceuticals may be sterilised by passage though a filter having a pore size of not more than 0.2 μm. However this cannot be used in the case of suspensions as the required particle size in these formulations (typically 2-5 μm) is significantly greater than this filter pore size. Similarly, pharmaceuticals may generally be sterilised by gamma-irradiation, but Budesonide, for example, is destroyed by such treatment (see for example, WO 00/25745). Cold sterilisation using ethylene oxide and carbon dioxide is also known, but stability of Budesonide under these sterilisation conditions has yet to be demonstrated. No further methods for the sterilisation of pharmaceuticals are currently acceptable to regulatory agencies.

Drugs typically provided as nebule suspensions are the steroids Fluticasone and Budesonide, which are used to treat asthma and chronic obstructive pulmonary disorder. These drugs are very insoluble in water and are sold as non-sterile powders.

A method of sterilising dry, powdered Budesonide is known from WO 99/25359. This method of sterilisation is, however, problematic as it requires Budesonide powder to be sterilised and then mixed with the other components of the formulation under sterile conditions. The drug formulation is subsequently prepared under sterile conditions.

International Application No. PCT/GB03/00702 (incorporated herein by reference) describes a solvent based sterilisation method for sterilising pharmaceuticals, in particular suspensions of drugs for use in nebulizers. A sterile composition of a pharmaceutical compound is prepared by combining solvent with a non-sterile pharmaceutical compound to form a solution, and then filtering the solution to yield a sterile pharmaceutical compound. All or part of the solvent is optionally removed to form a suspension, and under sterile conditions the compound is combined with a pharmaceutically acceptable carrier.

In order to be effective in the lungs, the particle size of an active ingredient in a suspension must be within a certain size range—typically the mass median diameter of the particles in the suspension is less than 10 μm. The sterile suspension may, therefore, be passed through a particle-size reduction apparatus, such as a homogenizer, Microfluidizer®) or similar device to reduce the average mass median diameter of the particles.

A suitable device, referred to as a Microfluidizer®), is available from Microfluidics, Inc. (MFIC), described in WO 99/07466 (incorporated herein by reference). Examples of Microfluidizer®) apparatus suitable for production scale particle-size reduction of a pharmaceutical suspension include the M-610 and M-210EH series machines. However, these devices cannot be sterilised.

Particle-size reduction apparatus such as the Microfluidizer®) apparatus typically operate under high pressures and comprise a plunger and a seal to separate the high pressure end of the apparatus from the low pressure end.

It is extremely important that the plunger seal maintains its integrity throughout the particle-size reduction process because if the seal were to fail, the sterility of the process could be compromised. The seal is therefore a high maintenance component that needs to be regularly removed for inspection and/or replaced.

Prior art apparatus is routinely supplied with more than one (most often two) interaction chambers arranged in series; with the first interaction chamber having internal conduits of the smallest size, having a circular cross-section with a diameter in the range from 10 μm, preferably 30 μm to 150 μm, more preferably to 100 μm; and the second interaction chamber having internal conduits of larger size, having a circular cross-section with a diameter in the range from 200 μm, preferably 300 μm to 600 μm, more preferably to 500 μm. For example, the M-120EH machine is supplied with interaction chambers in which the first chamber has conduits with dimensions down to approximately 78 μm and the second chamber with dimensions down to approximately 400 μm.

Our co-pending application (International Application No. PCT/GB04/03574), addresses some of the disadvantages discussed above. In particular, a sterilisable particle-size reduction apparatus is described, along with component parts that help sterilisation to be achieved. This apparatus can, therefore, be used for the production of a sterile suspension of a drug, such as Budesonide, for use in a nebulizer.

However, the apparatus described in PCT/GB04/03574 and other prior art apparatus have the disadvantage that they can become blocked, for example, by particles of the suspended material. Particularly susceptible to becoming blocked are component parts that contain flow passages/conduits having relatively small transverse cross-sectional area, such as an interaction chamber, which is used to reduce the size of particles in a suspension (described in more detail later).

For example, in order to achieve a sufficient degree of comminution and an appropriate size distribution and morphology, the recommended particle-size reduction method using the prior art Microfluidizer®) apparatus employs an interaction chamber having three 87 μm diameter, circular flow passages (i.e. having a transverse cross-sectional area of approximately $5.9\times10^3$ $\mu m^2$).

It is important to minimise the possibility of a particle-size reduction apparatus becoming blocked because blockages can be difficult to detect, especially when using interaction chambers containing more than one flow passage, and blockages can prevent the complete sterilisation of the apparatus.

A further disadvantage of prior art methods that employ relatively small diameter flow passages, e.g. 87 µm diameter, circular flow passages as discussed above; is that such methods optimally require the use of high pressure pumps (generating up to 210 MPa [30,000 psi]), to force suspension around the apparatus. Such high-pressure pumps can be difficult to sterilise.

It is an object of the invention to overcome or at least ameliorate problems associated with the prior art apparatus.

It has now surprisingly been found that an acceptable reduction in particle size, as well as a suitable particle size distribution may be achieved using one or more interaction chambers having flow passages that are substantially larger than was hitherto considered to be necessary.

SUMMARY OF THE INVENTION

The present invention thus provides a method of producing a comminuted suspension of particles, which comprises:
subjecting a suspension of particles to a comminution procedure carried out in a sterilised particle-size reduction apparatus;
said particle size reduction apparatus comprising at least one interaction chamber for reducing the particle size of the suspension, the or each interaction chamber being provided with a flow passage through which the suspension is forced, and an intensifier for forcing the suspension through the flow passage of the interaction chamber or interaction chambers, and
recovering a suspension of particles of reduced size;
characterised in that the transverse cross-sectional area of said flow passage is not less than $3.1 \times 10^4$ µm$^2$.

In a preferred embodiment of the invention the transverse cross-sectional area of the flow passage is in the range of $3.1 \times 10^4$ to $2.8 \times 10^5$ µm$^2$. More preferably, the transverse cross-sectional area of the flow passage is in the range of $4.9 \times 10^4$ to $2.0 \times 10^5$ µm$^2$, and most preferably in the range of $7.1 \times 10^4$ to $1.3 \times 10^5$ µm$^2$.

A further advantage of the method of the invention is that it can be carried out at lower pressure than typical particle-size reduction methods using prior art apparatus, which operate at "high pressure" (up to 210 MPa [30,000 psi]). Accordingly, there is provided a method of producing a comminuted suspension of particles, wherein a suspension of particles is forced from the intensifier at a pressure not exceeding 69 MPa (10,000 psi). More preferably, the pressure at which suspension is forced from the intensifier is in the range of 21-48 MPa (3,000-7,000 psi), still more preferably in the range of 28-41 MPa (4,000-6,000 psi), and most preferably at a pressure of approximately 34 MPa (5,000 psi).

The method of the invention can comprise multiple rounds of comminution in order to produce a comminuted suspension of particles of the desired size. Accordingly, there is provided a method of producing a comminuted suspension of particles, which comprises:
(a) subjecting a suspension of particles to a comminution procedure carried out in a sterilised particle-size reduction apparatus; said particle-size reduction apparatus comprising at least one interaction chamber for reducing the particle size of the suspension, the or each interaction chamber being provided with a flow passage through which the suspension is forced, and an intensifier for forcing the suspension through the flow passage of the interaction chamber or interaction chambers; to obtain a comminuted suspension of particles; characterised in that the transverse cross-sectional area of said flow passage is not less than $3.1 \times 10^4$ µm$^2$;
(b) optionally recovering a comminuted suspension of particles from step (a);
(c) subjecting a comminuted suspension of particles from step (a) to at least one further comminution procedure carried out in a sterilised particle-size reduction apparatus as defined in part (a); and
(d) recovering a comminuted suspension of particles of reduced size.

In preferred embodiments of the above method up to 50 comminution procedures are carried out. More preferably, the number of comminution procedures carried out is in the range of 10 to 50, 14 to 40 and 20 to 30.

In order to determine when particles of the desired size have been produced, there is provided a further embodiment of the above method, which comprises: recovering a comminuted suspension of particles after one or more further comminution procedures, measuring the size of recovered particles, and on the basis of the measured sizes, subjecting the suspension to one or more further comminution procedures, if necessary.

The above methods are suitable for producing a comminuted suspension of particles. Typically, the mass median diameter of particles in the recovered suspension of particles is in the range of 1-10 µm, preferably in the range of 1-5 µm and more preferably, the mass median diameter of particles in the recovered suspension of particles is in the range of 2-3 µm.

The invention further provides a modification of the above methods wherein the interaction chamber and the intensifier are integrally combined into a pump.

In accordance with a further object of the invention, there is also provided a sterilisable particle-size reduction apparatus. Said sterilisable particle-size reduction apparatus, comprising:
at least one interaction chamber for reducing the particle size of the suspension, the or each interaction chamber being provided with a flow passage through which the suspension is forced; and
an intensifier for forcing the suspension through the flow passage of the interaction chamber or interaction chambers;
characterised in that the transverse cross-sectional area of said flow passage is not less than $3.1 \times 10^4$ µm$^2$.

Although interaction chambers of the sterilisable particle-size reduction apparatus may be arranged in any suitable combination, e.g. in parallel or in series; a preferred sterilisable particle-size reduction apparatus of the invention comprises from 1 to 4 interaction chambers arranged in series. More preferably, the apparatus comprises a first and a second interaction chamber arranged in series.

Furthermore, while each interaction chamber may be provided with one or more flow passages/conduits e.g. 1, 2, 3, 4 or 5; in accordance with a preferred embodiment, the interaction chambers are provided with a single flow passage. Such an arrangement has the advantage that any blockages that may occur can be more easily detected.

Thus, a preferred sterilisable particle-size reduction apparatus comprises a first and a second interaction chamber arranged in series, wherein each interaction chamber is provided with a single flow passage.

In certain embodiments of the invention, the transverse cross-sectional area of the flow passage(s) of said first interaction chamber is approximately the same as the transverse cross-sectional area of the flow passage(s) of said second interaction chamber. Preferably, however, the transverse cross-sectional area of the flow passage(s) of said first interaction chamber is greater than the transverse cross-sectional area of the flow passage(s) of said second interaction chamber. In a more preferred embodiment, the transverse cross-sectional area of the flow passage of said first interaction chamber is approximately $1.3 \times 10^5$ μm², and the transverse cross-sectional area of the flow passage of said second interaction chamber is approximately $7.1 \times 10^4$ μm².

Typically, the flow passage/conduit is circular in cross-section. Accordingly, said flow passage/passages preferably have a maximum transverse diameter which is not less than 200 μm; more preferably the maximum transverse diameter is in the range of 200-600 μm; still more preferably in the range of 250-500 μm; and most preferably in the range of 300-400 μm.

The particle-size reduction apparatus may be any device that achieves reduction of the mass median diameter of particles in a suspension. In a particular embodiment, the apparatus is a Microfluidizer®)—suitably model M-110, M-610, or M-210EH, adapted according to the invention to be sterilisable.

Particular adaptations are set out below, and described in more detail in a specific embodiment of the invention. In general, to be sterilisable, apparatus of the invention comprise at least one, preferably two or more of the following features:
(1) there is no conduit between the output and input of the intensifier other than via the interaction chamber;
(2) valves in conduits between the intensifier and the interaction chamber are diaphragm needle valves;
(3) non-return valves in the apparatus have metal-to-metal seats;
(4) the plunger seal in the intensifier is adapted to be sterilised;
(5) the bushing assembly in the intensifier allows access of sterilising steam or water to the plunger seal;
(6) the cam nut in the intensifier is adapted to be sterilised;
(7) a rupture disc is used as a pressure relief valve; and
(8) a seal is provided to prevent suspension from reaching the driving fluid that drives the intensifier in the event of failure of the plunger seal.

By "sterilisable" it is meant that sterility sufficient to satisfy MCA and FDA regulations for pharmaceutical use is achieved. By way of example, at the present time, the MCA requires a 6-log reduction in suitably heat-resistant bacterial spores (e.g. *Geobacillus stearothermophilus*, ATCC No. 7953) to be demonstrated—that is, the number of spores present after sterilisation is reduced by 6 log in comparison to the number of spores present before sterilisation. In one embodiment, to demonstrate sterilisation, a challenge of heat-resistant bacterial spores in excess of 1 million is administered and then sterilisation carried out. If total kill of spores is demonstrated then sterilisation has been achieved. The FDA may allow an extrapolation of sterility from a short time period. Hence, if a 3-log reduction is demonstrated in x minutes then the FDA may allow an extrapolation to a 6-log reduction in 2x minutes.

By "high pressure" it is meant pressures in excess of 69 MPa (10,000 psi), preferably in excess of 138 MPa (20,000 psi) and more preferably up to around 217 MPa (30,000 psi). Prior art apparatus typically operate using oil at a pressure of up to 34 MPa (5,000 psi) to drive a piston in the intensifier, resulting in a pressure in the plunger barrel of the intensifier of up to 217 MPa (30,000 psi). Hence, suspension exits the plunger barrel of the intensifier at this pressure and is directed to the interaction chamber or chambers. On exiting the last interaction chamber the pressure of the suspension has typically reduced to below about 0.69 MPa (100 psi).

The apparatus of the present invention can operate at far lower pressures than the apparatus of the prior art. For example, in a preferred embodiment, suspension exits the plunger barrel of the intensifier at a pressure of 34 MPa (5,000 psi). However, even at such low pressures, due to the relatively large flow passage(s) of the apparatus of the invention, a greater volume of suspension can be processed in a defined period of time, than can be processed by apparatus and methods of the prior art, that require far higher pressure, e.g. up to 217 MPa (30,000 psi).

For example, a sterilisable particle-size reduction apparatus of the invention, which comprises a single interaction chamber having a single flow passage with a circular cross-section of diameter 400 µm, can process approximately 1600 ml/min of suspension at 34 MPa (5,000 psi). Therefore, a typical batch of 12 liters of suspension can be subjected to 20 rounds of comminution in 150 minutes.

A suitable pump for use in the apparatus and methods of the present invention is a diaphragm pump. An advantage of using a diaphragm pump is that it can be more easily sterilised than a high-pressure pump.

The intensifier suitably comprises an output and an input, and the interaction chamber comprises an input and an output, the output of the intensifier being connected to the input of the interaction chamber and the output of the interaction chamber being connected to the input of the intensifier, and there is no conduit between the output of the intensifier and the input of the intensifier other than via the interaction chamber. This means that all the suspension leaving the intensifier at must travel through the interaction chamber, in which particle-size reduction takes place, before exiting the apparatus. In particular this means that the sterilisable particle-size reduction apparatus of the present invention does not comprise a bypass line that would allow product (and sterilising steam or water) to bypass the interaction chamber, as the presence of such a line means that this section of the apparatus cannot be sterilised.

In the apparatus and methods of the present invention, it has been found that best results are achieved, in reducing the particle size of a suspension of Budesonide, when the suspension exiting the intensifier passes first into a interaction chamber with larger flow passage/conduit size and then into an interaction chamber with smaller flow passage/conduit size.

The intensifier and interaction chamber(s) are linked by conduits, and the conduits are generally provided with a number of valves to control or direct flow of material. In one embodiment, the valves in the conduits between the intensifier and the interaction chamber are sterilisable diaphragm needle valves. Other valves in the apparatus are non-return valves, which prevent flow of suspension in the wrong direction—that is, the non-return valves ensure a flow of product in one direction from the intensifier to the interaction chamber. Preferably, the non-return valves in conduits between the intensifier and the interaction chamber(s) have metal-to-metal seats. The provision of metal-to-metal seats enables effective sterilisation of the non-return valves in situ.

In particular apparatus, the intensifier comprises a bore and a reciprocating plunger and a seal between the plunger and the bore. The purpose of the seal is to separate the higher pressure side of the intensifier from the lower pressure side. In prior art apparatus, the seal must be able to withstand high pressures (up to 210 MPa [30,000 psi]), without extruding or otherwise failing. This is not such an important factor in the apparatus and methods of the present invention. Nevertheless, a preferred seal, used in apparatus of the invention, is adapted to be sterilisable, preferably incorporating a brace to prevent sides of the seal from collapsing, which brace is made of or comprises a resilient plastics material. The seal is described in more detail below.

In other particular apparatus, the intensifier comprises a reciprocating plunger and a bushing assembly to guide the plunger as it reciprocates within the plunger chamber or barrel. The bushing assembly preferably comprises a bushing holder and a bushing supported within the bushing holder. This bushing assembly preferably comprises a channel in or on the surface of the bushing assembly, to allow sterilising steam or water to pass through the bushing assembly whilst the plunger is in place. The channel in or on the surface of the bushing assembly may typically be a groove or a conduit, and may be located on the outer or inner surface of the bushing and/or on the bushing holder. The groove or conduit may be of any reasonable dimensions and there may be any number of grooves or conduits, enabling steam or water to pass through the bushing assembly whilst the plunger is in place. This bushing assembly means that sterilising steam or sterilising water has access through the bushing to components of the apparatus that would otherwise be difficult or impossible to sterilise, and this arrangement especially allows access of sterilising water or steam to the back of the plunger seal.

Referring to the apparatus in the figures, one end of the intensifier plunger is connected via a threaded cam nut to a connecting rod having a screw thread to receive the cam nut. The dimensions of the screw thread and the thread of the cam nut are such that as the nut is screwed onto the connecting rod (con rod), respective mating surfaces on the cam nut and the con rod mate simultaneously, which avoids nooks and crannies that may harbour microorganisms and thus renders this portion of the apparatus sterilisable. The plunger in use bears on the front end of the con rod and is held loosely in place by the cam nut. As the plunger is driven in one direction, the cam nut approaches and then hits and triggers an air switch, changing the direction of flow of oil from oil lines to the piston around the con rod and sending the plunger back in the reverse direction.

Optionally, a heat exchanger is provided to control the temperature of the suspension and preferably to maintain it at from 7° C. to 40° C. in use. If the suspension is a drug suspension, it is important to maintain the temperature within a certain range because some drugs are susceptible to heat degradation. By way of example, Budesonide may be degraded by long exposure to temperatures above 40° C., so during Budesonide processing the temperature is preferably maintained below 50° C., more preferably below 40° C. The apparatus and methods of the present invention have a further advantage that heating of the apparatus during the comminution procedure is greatly reduced from that of prior art methods and therefore, use of a heat exchanger during comminution may not be necessary.

A further use of the heat exchanger is during sterilisation of the apparatus. Time is spent heating various components of the apparatus up to the sterilising temperature. Therefore, in a preferred method of sterilisation, the heat exchanger is used to heat the interaction chamber or chambers, and preferably also the piping immediately surrounding the chambers, to reduce the time required for the interaction chambers to reach the required temperature. In a further preferred embodiment, the apparatus comprises a first heat exchanger to maintain the temperature of the suspension in the interaction chamber and a second heat exchanger to maintain the temperature of the suspension in the intensifier, wherein the first and second heat exchangers are independently controlled.

The apparatus optionally comprises at least one pressure relief valve, so that if excessive pressure builds up on the low pressure side of the apparatus, that is to say downstream of the interaction chamber, this pressure can be relieved instead of leading to damage of the low pressure side. The valve is preferably a rupture disc. By rupture disc it is meant a valve that bursts if the pressure at the valve exceeds a certain value. Hence, the rupture disc acts as a safety mechanism, to alert an operator to the fact that a pressure exceeding the specified value has been reached at that point in the apparatus. This could typically occur if one of the non-return valves of the apparatus has failed or if there is a blockage in the return line. In one embodiment, the rupture disc will burst if the pressure at the disc exceeds 150 psi. In another embodiment, the rupture disc is positioned so as to prevent damage to the interaction chamber and associated pipework and valves should the plunger seal fail.

During operation of the apparatus, once the apparatus has been sterilised it is used to reduce the particle size of a sterile suspension. If there were to be a failure, possibly a transient failure, leading to excess pressure on the low-pressure side of the apparatus then rupture of the disc alerts the operator to the failure. In this event, the suspension in the apparatus is then discarded, as the failure could lead to contamination, and the risk of producing a non-sterile suspension. Hence, an advantage of using this rupture disc is that a transient failure, which in the art would be accommodated by transient opening and closing of a standard relief valve, does not mask a failure of sterility in the apparatus and hence in the suspension being processed.

Particular apparatus further comprise a seal that prevents suspension from reaching the driving fluid that drives the intensifier in the event of failure of the plunger seal. It is advantageous to prevent suspension from interfering with the hydraulic pump section of the apparatus if the plunger seal fails. This seal is typically capable of withstanding pressures of 1 MPa (150 psi) at 200° C. while the plunger is moving. Preferably, this seal is a lip-type seal and is manufactured from PTFE. The seal may further comprise a coiled metal support inner spring to help avoid collapse, extrusion or distortion at high temperature.

In an example of using the apparatus, product is processed in several cycles. In each cycle, product is passed from a feed tank into the particle-size reduction apparatus. As the cycle progresses, product accumulates in a recycle tank. Once the feed tank is empty or nearly empty, a cycle is deemed to be finished, and the feed tank is then re-filled from the recycle tank, indicating that a further cycle is beginning. We have circulated a suspension of Budesonide in water and Tween up to 50 times at 34 MPa [5,000 psi] (depending on the selection and arrangement of interaction chambers used), in order to achieve a desired particle size distribution of 2-3 μm. It is possible to circulate the suspension with the apparatus operating at lower or higher pressure (e.g. 7-69 MPa [1,000-10,000 psi]), in which case a larger or smaller number of cycles, respectively, would be required to achieve the same particle size distribution for a given combination of interaction chambers.

The apparatus of the present invention may comprise modified components, as described in our co-pending patent application (International Application No. PCT/GB04/03574), which is incorporated herein by reference. For example, one such useful component is a modified bushing assembly for use with a cylindrical plunger, comprising a bushing holder and a bushing, held in place by the bushing holder, wherein the bushing assembly comprises one or more conduits to allow passage of sterilising steam or water therethrough.

International Application No. PCT/GB04/03574 also provides a bushing assembly for a plunger that reciprocates in a plunger barrel, comprising a bushing holder which attaches to a neck of the barrel and a bushing held in situ by the bushing holder and which guides the plunger into and out of the barrel, wherein the bushing and/or the bushing holder comprises one or more conduits to allow passage of sterilising steam or water through the bushing assembly.

During sterilisation of the apparatus, the conduits allow access of sterilising water or steam to parts of the apparatus that might otherwise be difficult or impossible to sterilise. In particular, sterilising water or steam can now have access to the plunger seal. During sterilisation, sterilising water or steam passes through the bushing assembly and sterilises the back of the plunger seal. Usually, whilst sterilisation is taking place, the apparatus is run at a reduced rate, enabling sterilisation of all parts of the intensifier, both the high-pressure side and the low-pressure side, the high-pressure side being sterilised by steam introduced directly into the plunger barrel.

The plunger barrel may, for instance, be the plunger barrel of a particle-size reduction apparatus, such as a Microfluidizer®).

By conduits with respect to the bushing holder described above, it is meant grooves, channels or the like through which the steam or water may pass. The grooves or channels may be of any reasonable dimensions, so long as passage of the steam or water therethrough is permitted.

Said grooves/channels may be located anywhere on the outer or inner surface of the bushing and may be aligned in any direction, so long as they permit passage of steam or water through the bushing assembly. For example, the bushing may comprise one or more grooves located on its outer surface. Alternatively, or in addition, said bushing may comprise one or more grooves located on its inner surface. The grooves may be parallel to the longitudinal axis of the bushing or said grooves may be formed in a spiral around the longitudinal axis of the bushing.

It is an option for the bushing assembly to comprise a bushing which comprises one or more grooves and a bushing holder which comprises one or more grooves or one or more conduits to allow passage of steam or water therethrough.

Where both the bushing and the bushing holder comprise one or more grooves, it is preferred that said one or more grooves of said bushing and bushing holder are in alignment as this enables unhindered passage of steam through the bushing apparatus. Alignment of said one or more grooves of the bushing and the bushing holder can be achieved using a bushing assembly wherein said bushing further comprises one or more projections that cooperate with one or more recesses in said bushing holder in order to align said one or more grooves of said bushing with those of the bushing holder. Alternatively said bushing holder has one or more projections that cooperate with one or more recesses in the bushing.

Co-pending patent application (International Application No. PCT/GB04/03574) also provides an annular high-pressure seal that may be used in the apparatus of the present invention. This high-pressure seal for a plunger reciprocating within a barrel, comprises lower and upper body portions, said upper portion being in the form of a cup and having sides surrounding a recess, the sides being outwardly deformable so that respective outer and inner edges of the sides of the cup make, in use, sealing contact with respectively the barrel and the plunger. The seal further comprising a brace to prevent the sides from collapsing into the recess under low pressure and wherein the brace comprises a resilient plastics material. This "high-pressure seal" is capable of withstanding pressures typically encountered in a particle-size reduction apparatus. Typically, a high-pressure seal can withstand pressures of up to 34 MPa (5,000 psi), preferably up to 69 MPa (10,000 psi), more preferably up to 138 MPa (20,000 psi), and still more preferably, up to 210 MPa (30,000 psi). Such a high-pressure seal is also sterilisable.

By "sterilisable" it is meant that sterility sufficient to satisfy MCA and FDA regulations for pharmaceutical use (as outlined above with relation to sterility of the particle-size reduction apparatus) is achieved.

The seal employed in the apparatus and methods of the present invention (described in International Application No. PCT/GB04/03574), confers the advantage that it can be sterilised, an especially important feature as the seal comes into contact during operation of the apparatus with suspension on the high-pressure side of the apparatus. In comparison, some prior art seals contain structural and surface features that harbour microorganisms, rendering such seals incapable of sterilisation, and these features are avoided in the seal used in the invention.

The brace of the plunger seal presents a smooth surface free from cavities. By free from cavities it is meant free from holes, cracks, gaps or other spaces in the otherwise solid mass of the brace. Minimising (and preferably eliminating) cavities in which microorganisms may collect, ensures that complete sterilisation of the seal can take place.

The resilient plastics material of the brace is disposed in the recess between the cup sides of the plunger seal. The plastics material can fill the recess of the plunger seal so that the upper surface of said plastics material is level with or nearly level with the height of the cup sides, i.e. the upper surface of said plastics material reaches at least two thirds the height of the cup sides.

The plunger seal may further comprise a metal spring; if so this is preferably enclosed within the resilient plastics material of the brace. Using a metal spring adds further strength or resilience to the brace of the seal, and enables choice of alternative plastic materials for the brace.

Usually, the plunger seal is operable at temperatures up to 75° C., preferably at temperatures up to 90° C., most preferably at temperatures required for sterilisation of the apparatus, generally up to about 122° C. The plunger seal material may be virgin PTFE or glass-strengthened PTFE. These materials are known to be capable of withstanding high pressures and temperatures without extruding. An example of glass-strengthened PTFE from which seals of the invention can be made is Rulon®).

It is preferred that the plunger seal brace is manufactured from a different material to that of the other seal components, so that the cup sides of the seal will deform outwardly under the pressures experienced during operation of the apparatus and form sealing contact with the plunger and the bore, but under low pressure, e.g. whilst the machine is at rest, the cup sides do not collapse inwardly leading to subsequent seal failure. The resilient plastics material of the brace is preferably more flexible than the material of the upper and lower body portions of the seal. It is, however, an option for the brace to be manufactured from the same material to that of the other seal components, so long as the seal remains outwardly deformable in use.

Preferred apparatus for use in the methods of the invention, and component parts therefor, are substantially free of niches which can harbour microorganisms and/or their spores or which can shield them from the effects of the sterilising steam and/or water during sterilisation of the apparatus and its parts. For example, the apparatus preferably avoids unnecessary pipework or pipework containing dead-ends or inaccessible spaces that would represent such niches and compromise sterility or validation thereof.

The present invention further provides methods of sterilising a particle-size reduction apparatus. A first method comprises the step of charging the particle-size reduction apparatus of the invention with steam, to achieve sterilisation.

A sterilisation protocol may optionally be followed by a method of validating sterilisation—in order to ensure that the sterilisation is effective and/or complete.

In a particular embodiment of the present invention, sterilisation is deemed to have occurred when a protocol, previously demonstrated to achieve a 6-log reduction in heat resistant bacterial spores is followed.

Generally, validation of sterility is carried out in order to establish a protocol that is demonstrated to result in a sterile apparatus, which apparatus is then used to reduce the particle size of a sterile suspension. Validation of sterility is not then routinely carried out with every batch, but may be used as part of regular maintenance of the apparatus or to carry out spot checks on individual batches of suspension.

When sterilising the particle-size apparatus using steam, it has been found advantageous to insulate the valves and conduits downstream of the interaction chamber, so as to maintain steam temperature during sterilisation. Loss of heat from the steam can cause undesirable condensation and loss of effective sterilisation.

Referring to a specific embodiment of the invention, described in more detail in the examples, steam traps are used around the apparatus, located in places where condensate would develop and risk accumulating. The steam traps are open when the temperature is below 121° C. but during sterilisation the traps are open until they have reached the sterilising temperature, generally 121° C., at which point they close. If the temperature in a trap drops, for example due to accumulation of condensate, the trap opens, releasing the condensate from the apparatus, and then will close again when the temperature has reached 121° C. Thus during sterilisation, traps are continually opening and closing.

Temperature probes are used all around the apparatus to provide a temperature map of the apparatus and to confirm that the temperature in all relevant places is at least 121° C. The probes are connected to a central monitoring unit, so that the duration of the sterilisation procedure is timed from the point at which all relevant parts of the machine have reached the sterilising temperature.

During sterilisation the following steps are typically carried out:
  steam traps are connected;
  temperature monitors are connected;
  steam is introduced into the apparatus, optionally with the apparatus running;
  temperature is monitored at each monitor until all have reached the sterilising temperature, generally 121° C.;
  during this period, the steam traps start in the open position but close as they reach 121° C., opening and closing as described above;
  the time at which temperature recorded by each of the temperature monitors has reached the sterilising temperature is noted;
  once all monitors have reached 121° C. then the sterilisation is continued by continuing to introduce steam into the apparatus for a predetermined period of time, this time being determined empirically.

The number of steam traps connected to the apparatus varies with the type of apparatus and depends on the particular sterilisation protocol being carried out. We have achieved good results using an M-210EH Microfluidizer®) with up to 20 steam traps, but it is an option to use fewer steam traps, for instance up to 10, but preferably at least 5 steam traps are used.

The number of temperature monitors connected to the apparatus varies with the type of apparatus used. We have achieved good results using an M-210EH Microfluidizer®) with up to 10 temperature monitors, though it is an option to use fewer temperature monitors, for instance about 5 temperature monitors, or more temperature monitors, for instance, up to 20.

When the apparatus is allowed to run during introduction of steam, the apparatus is run at a slow speed. When an M-210EH Microfluidizer®) is used, steam is introduced at a speed of typically up to half the running speed of the apparatus, and in some embodiments, up to a third of the running speed of the apparatus.

In a particular embodiment, this period is determined by introducing heat resistant bacterial spores into the apparatus, introducing steam into the apparatus and monitoring apparatus temperature until it has reached the sterilising temperature; continuing to introduce steam for a first known amount of time; determining whether after that first known amount of time sterilisation has been achieved; and if sterilisation has not been achieved, repeating the method for a second, longer known amount of time.

In practice, a protocol is determined that is accepted as ensuring sterilisation after a given period of time, and this time is noted and a margin of error, such as an additional at least 5, 10 or 20 percent of the noted time, is added and this modified protocol is noted as the sterilising protocol. Also in practice, the intensifier tends to take longest to reach an acceptable sterilising temperature. The intensifier can be provided with a jacket or other insulation to help speed up this process.

As the apparatus of the present invention tends to generate less internal heat than prior art apparatus a heat exchanger may additionally be used to raise the temperature of the sterilising water or steam to an acceptable sterilising temperature.

During sterilisation, it is preferred that all steam exiting the intensifier passes through the interaction chambers—i.e. sterilising steam cannot bypass the interaction chambers, as this may risk creation of areas in the apparatus, around the chambers, which cannot be sufficiently reached by the steam to achieve sterilisation. A jacket is also optionally located around the interaction chambers. This jacket can be used to increase the temperature of the interaction chambers using steam to assist sterilisation and it can be used to cool the interaction chambers when the machine is operated.

Whilst sterilising the apparatus described in the examples, as steam is passed through the chambers it passes from a 3 mm diameter feed to a 0.087 mm feed, potentially resulting in trapped condensation at the interaction chamber exit. It is therefore preferred that steam is introduced into the intensifier and, in addition, downstream of the interaction chamber or chambers. This step assists in the rapid sterilisation of apparatus, conduits etc, located on the other side of the interaction chambers to the primary steam source. Pre-heating the interaction chambers can also serve to reduce the potential problem of trapped condensation at the interaction chamber exit.

A second method of sterilisation comprises charging the particle-size reduction apparatus of the invention with pressurised, superheated water so as to sterilise the apparatus.

When pressurised, superheated water is used for sterilisation, the intensifier can be operated so as to control the temperature of the water during sterilisation. Operating the intensifier leads to an increase in the pressure of the water within the apparatus, in turn leading to an increase in temperature which can be monitored. Hence, by adjusting pressure within the apparatus, temperature within the apparatus can also be adjusted and kept at or above a desired sterilising temperature of 121° C. Following a preferred embodiment of the water-based sterilisation method, water is introduced into the apparatus at a temperature below 100° C., and this could suitably be at room temperature, and the apparatus is then operated so as to increase the water temperature up to the desired sterilising temperature. Temperature monitors located on the apparatus are used to confirm that the desired temperature has been reached, at which point sterilisation is continued at or above this temperature for a time period previously determined to be accepted as resulting in sterilisation, this time period being determined empirically.

When pressurised, superheated water is used for the sterilisation method, it is preferred that steam is nonetheless used for sterilisation of the isolation area of the intensifier, and the method comprises charging the isolation area of the intensifier with steam, at a temperature the same as or higher than the temperature of the water, preferably at least 0.5° C. higher.

After sterilisation has been carried out, the water is cooled and, for example, Budesonide suspension and optional extra ingredients such as surfactants are added. One option is to sterilise the apparatus using super-heated water, then use sterile air to flush the system before introducing a Budesonide suspension. Another option is to sterilise the apparatus using super-heated water containing surfactant, cool the water and surfactant solution and then add the Budesonide suspension. In this way, the end of the sterilising step becomes the beginning of the priming step. Further, a filter can be used to collect microorganisms.

The present invention further provides a method of preparing a sterile suspension, in particular a sterile suspension comprising Budesonide or Fluticasone, comprising the steps of obtaining a sterile particle-size reduction apparatus, passing a sterile suspension through the sterile apparatus, and monitoring particle size in the suspension. Preferably, the particle-size reduction apparatus is sterilised according to the steam or water sterilisation methods of the present invention, as described above. In one embodiment, particle size in the suspension is monitored continuously as the suspension is passed through the apparatus. In another embodiment, particle size is monitored between discrete passes. The suspension is passed through the apparatus until the desired final mass median diameter of the particles is obtained—typically 2-3 μm. Once the desired particle size has been achieved, the sterile suspension may then be transferred from the apparatus to be packaged into sterile ampoules, preferably nebules.

In another aspect, the present invention also provides a sterile nebule containing a sterile suspension prepared according to the present invention. When the suspension in the nebule comprises Budesonide or Fluticasone, the sterile nebule may be of use in the treatment of asthma or chronic obstructive pulmonary disorder.

The sterility of components of the particle-size reduction apparatus of the invention can then be validated. For example, the sterility of a bore may be validated by the following method, which is carried out under sterile conditions. The method comprises the steps of removing a seal from the bore, under sterile conditions transferring the seal to growth medium, observing whether there is growth of microorganisms in the growth medium, calculating the number of microorganisms present, and thereby determining whether the bore is sterile. In a preferred embodiment, the method comprises the initial steps of inoculating the seal with a known quantity of heat-resistant bacterial spores, most preferably at least $1 \times 10^6$ heat-resistant bacterial spores, inserting the seal into the bore, and carrying out a sterilisation protocol as described above.

Sterility is judged according to the MCA and FDA guidelines. The component, such as a seal is typically incubated in the growth medium under conditions conducive to growth of microorganisms, and growth of microorganisms indicates that the seal (and hence the bore) has not been sterilised effectively. In a preferred embodiment, the validation method comprises the steps of inserting a component of the apparatus, such as a seal, inoculated with a known number of heat resistant bacterial spores into the apparatus (e.g. into the bore), carrying out a procedure intended to sterilise the apparatus including the bore, and then validating sterility of the component (e.g. the seal), and hence the bore or other component of the apparatus. The bore, for example, may be the bore of a particle-size reducing apparatus and, in one embodiment; the sterility of the bore may be used as an indication of sterility of the entire apparatus.

BRIEF DESCRIPTION OF THE DRAWINGS

The invention is now described in more detail with reference to the accompanying drawings, in which.

DETAILED DESCRIPTION OF THE INVENTION

Figure 1:
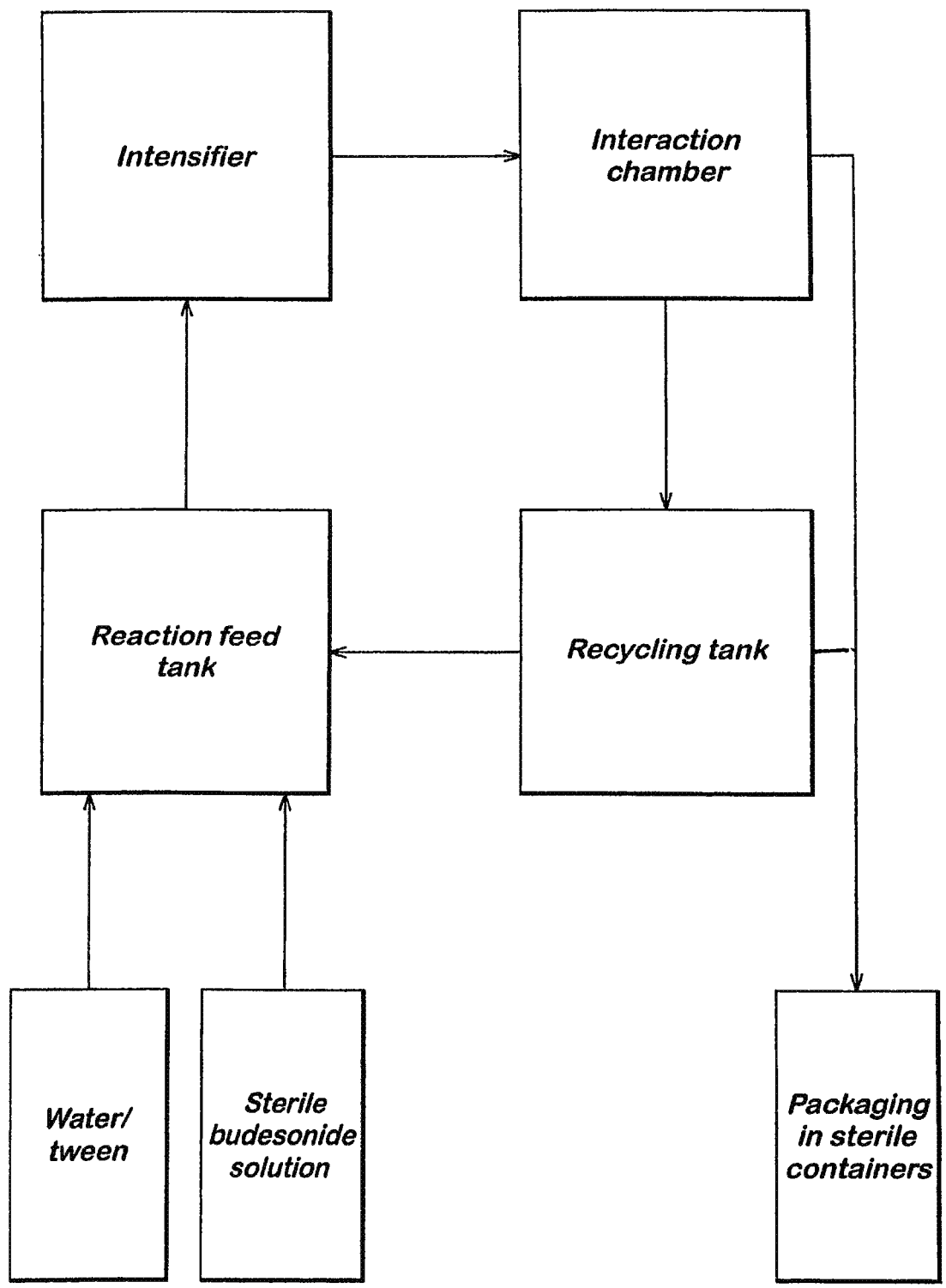
FIG. 1 is a schematic diagram showing flow of suspension between the component parts of a particle-size reduction apparatus.

Referring to the drawings in more detail; FIG. 1 is a schematic diagram showing flow of a sterile Budesonide suspension between the main component parts of the particle-size reduction apparatus. The suspension is generated in the reaction feed tank—by combining a sterile solution of Budesonide in alcohol with an aqueous solution comprising Tween and water. The sterile suspension is fed into the intensifier of the apparatus from the reaction feed tank via a conduit. The output from the intensifier leads, via a conduit, into the input of the interaction chamber. The interaction chamber has two outputs and hence, from the interaction chamber, the suspension may follow either of two routes. If particle size has been reduced to the desired final mass median diameter, the suspension leaves the apparatus for packaging in sterile containers, such as ampoules. If, however, particle size is still too large, the suspension leaves the interaction chamber and passes via a conduit into the recycling tank. The recycling tank then feeds the suspension back into the reaction feed tank, from which the suspension is fed back into the intensifier for another pass. Alternatively, product can be transferred from the recycling tank to be further processed and/or packaged.

As can be seen from FIG. 1, the suspension cannot pass from the output of the intensifier to the input of the intensifier without passing through the interaction chamber, because there is no conduit between the output of the intensifier and the input of the intensifier other than via the interaction chamber.

In practice, the particle-size reduction apparatus is run in almost discrete passes. Suspension from the interaction chamber that must be passed through the apparatus at least once more is fed into the recycling tank and accumulates there whilst the reaction feed tank empties. Only once the reaction feed tank is almost empty is suspension from the recycling tank fed back into the reaction feed tank for another pass.

Figure 2:
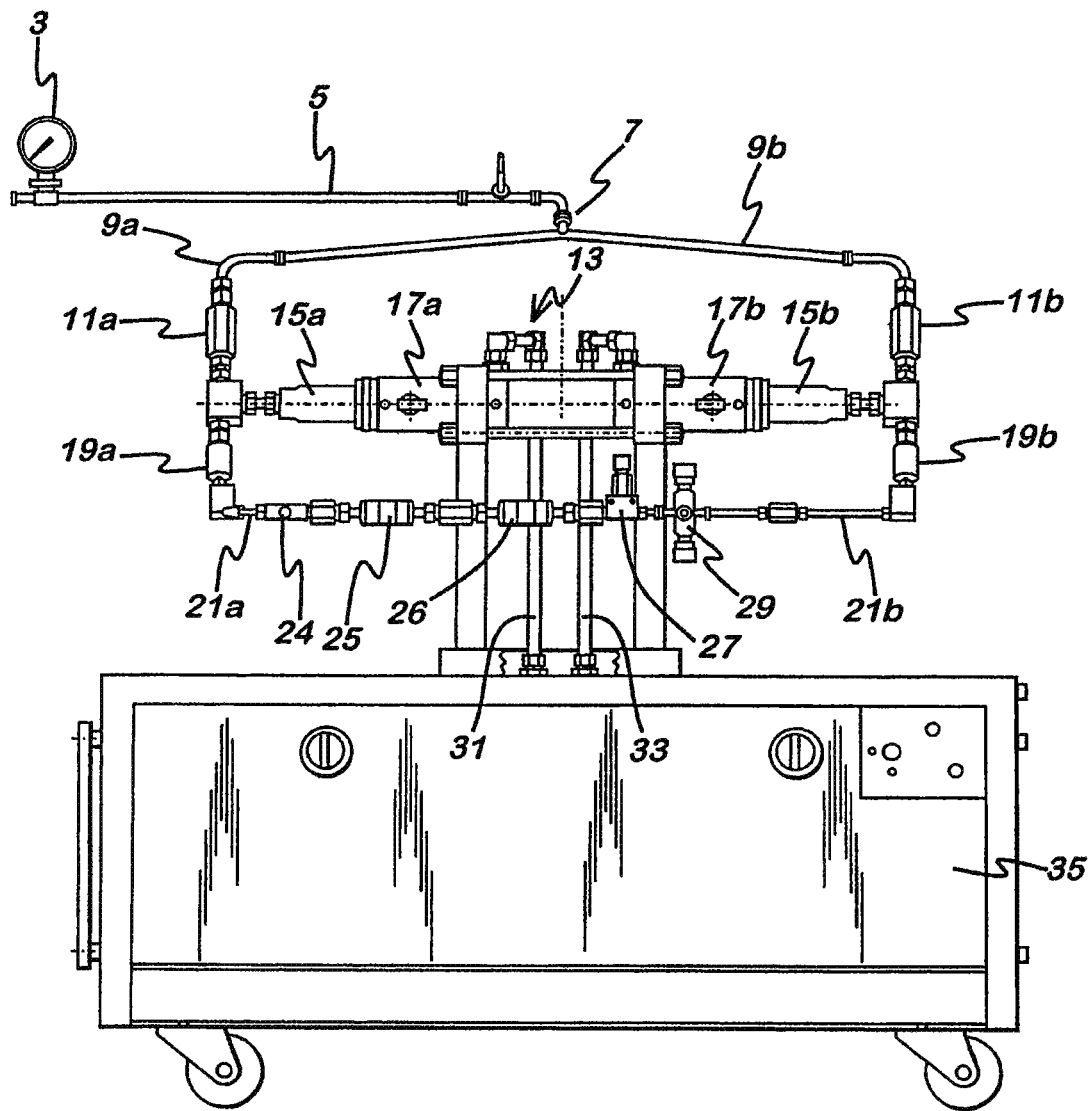
FIGS. 2, 3 and 4, respectively are front, top and side views of a Microfluidizer®) M-210EH apparatus that can be modified in accordance with the present invention.
Figure 3:
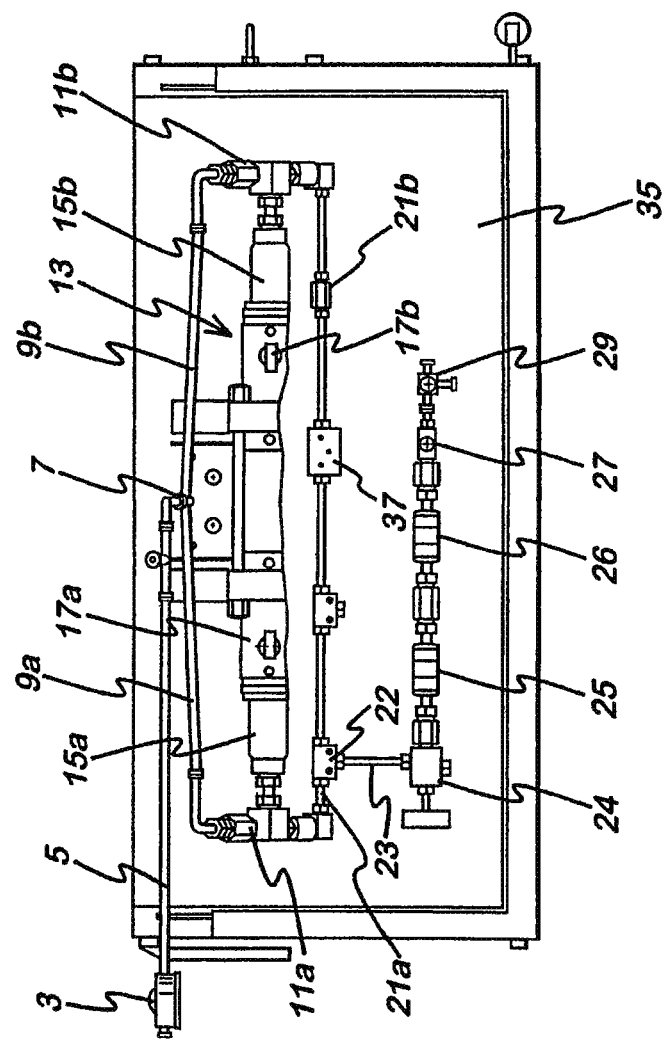
Figure 4:
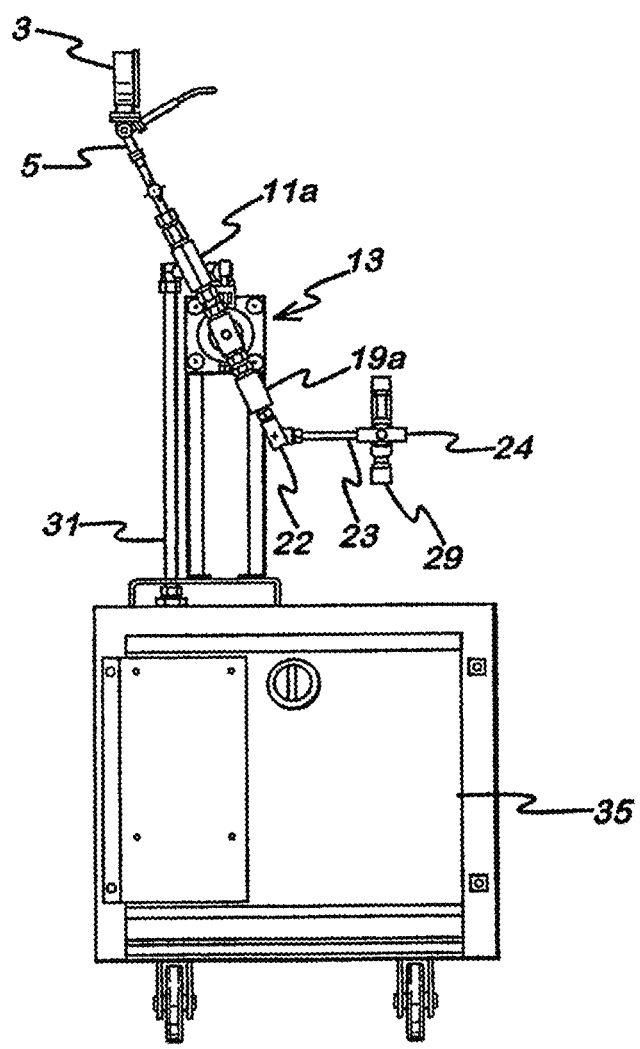
Figure 5:
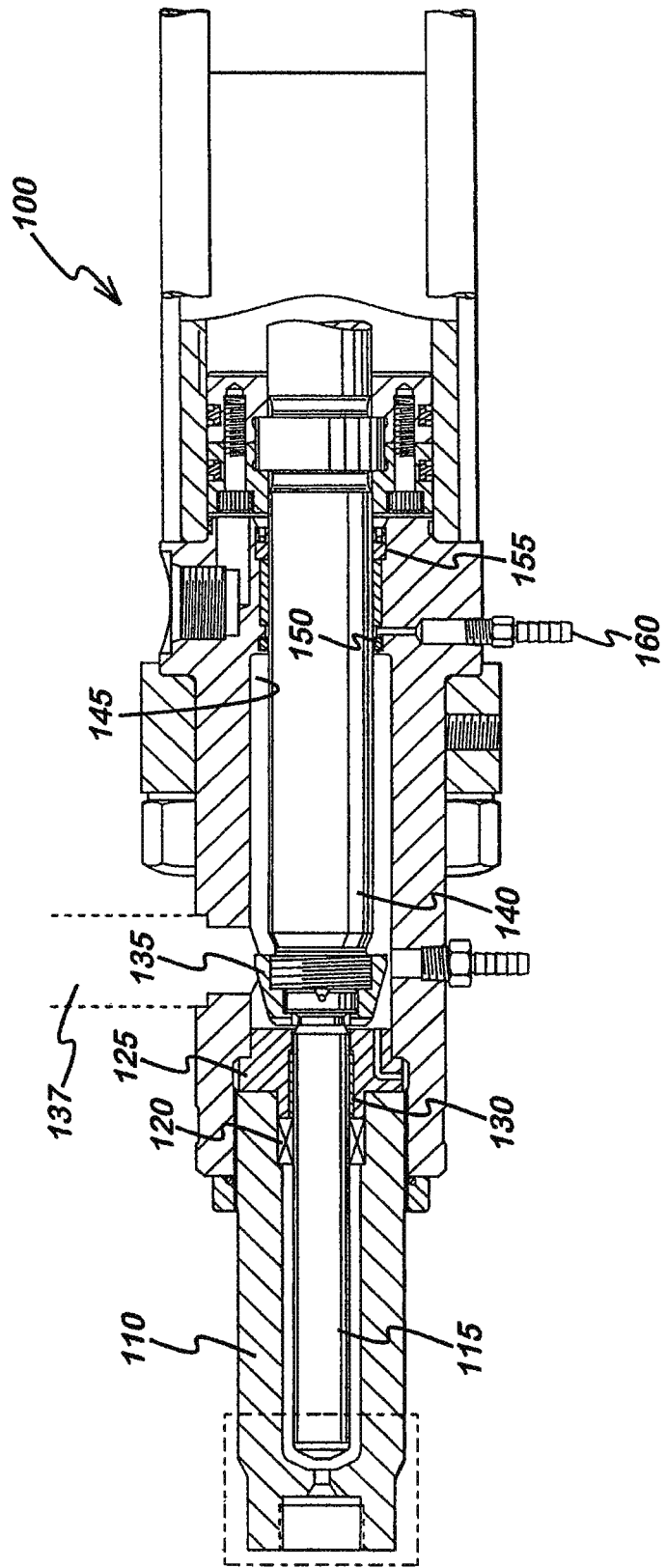
FIG. 5 is a cross-sectional view of the intensifier of a Microfluidizer®) M-210EH apparatus that can be modified in accordance with the present invention.

A Microfluidizer®) M-210EH particle-size reduction apparatus (1) modified according to one embodiment of the present invention is now described with reference to FIGS. 2-5. FIG. 2 shows a front view of the modified apparatus, FIG. 3 shows a top view and FIG. 4 shows a left side view.

The Microfluidizer®) comprises intensifier (13), interaction chambers (25 and 26) and base unit (35) housing an oil tank, pump and motor (not shown).

Sterile suspension enters the Microfluidizer®) from the reaction feed tank via input (3) and passes along conduit (5). At T-junction (7) the flow of suspension is split along two conduits (9*a* and 9*b*), which feed into opposite ends of the symmetrical intensifier (13) via non-return valves (11*a* and 11*b*). The non-return valves prevent the suspension from flowing back along conduits 9*a* and 9*b*, which might otherwise result due to the pressures created in the intensifier.

Suspension passes into the plunger barrels (15*a* and 15*b*) at each end of the intensifier. Suspension is prevented from entering the isolation chambers (17*a* and 17*b*) by plunger seals (not shown on FIGS. 2-4).

Each M-210EH series machine contains an on-board 15 horsepower electric-hydraulic module within base unit (35) that provides power to a double-acting intensifier plunger (not shown on FIGS. 2-4). The intensifier plunger amplifies the hydraulic pressure and, in turn, imparts that pressure to the product stream. The intensifier typically has a multiplier ratio of about 3:1 to 20:1. Process pressures ranging from 17 to 210 MPa (2,500 to 30,000 psi) may be selected. Preferably, a process pressure of approximately 5,000 psi is used. Therefore, the hydraulic module may be replaced by a diaphragm pump which can be sterilised more easily.

The intensifier plunger supplies the desired pressure at a constant rate to the product stream. As the plunger travels in one direction, it drives the suspension at constant pressure through the flow passage(s) in interaction chambers (25 and 26). As the intensifier plunger continues its travel in one direction, a series of check valves allow suspension to be drawn into the opposite end of the pump barrel. Oil lines (31 and 33) provide a flow of oil within the plunger barrels that regulates the direction of movement of the plunger within each plunger barrel. Thus, as the intensifier plunger completes its stroke, it reverses direction and the new volume of suspension is pressurised repeating the process. This creates a constant flow of suspension at near constant pressure through the interaction chamber.

Suspension at the desired pressure (e.g. 34 MPa [5,000 psi]) leaves each plunger barrel 15*a* and 15*b* of the intensifier via non-return valves (19*a* and 19*b*) respectively, and passes along conduits (21*a* and 21*b* respectively). A pressure transducer (37) on conduit 21*b* monitors pressure of the suspension as it passes along conduit 21*b*. Once the two flows of suspension along conduits 21*a* and 21*b* reach T-junction (22), the flows are combined in conduit (23).

From conduit (23), the pressurised suspension enters the interaction chambers (25 and 26) via diaphragm needle valve (24). It is within the interaction chambers that particle-size reduction occurs, as the suspension is forced through precisely defined fixed-geometry microchannels in the interaction chambers under the desired pressure (e.g. 34 MPa [5,000 psi]), creating shear and impact forces as the product stream impinges upon itself and on wear-resistant surfaces at high velocities. The flow passage(s) in the first interaction chamber (25) have a transverse cross-sectional area of not less than $3.1\times10^4$ $\mu m^2$, and the flow passage(s) in the second interaction chamber (26) also have a transverse cross-sectional area of not less than $3.1\times10^4$ $\mu m^2$, The combined forces of shear and impact within the microchannels act upon products to reduce mean particle size (mass mean diameter) and can reduce the mean particle size of a Budesonide suspension from approximately 50 μm to 2-3 μm in typically up to 50 passes through the Microfluidizer®) at 34 MPa (5,000 psi) However, more or less passes through the Microfluidizer®) may be required, e.g. from 10 to 50 passes, or more than 50 passes, depending on the combination of interaction chambers selected for the particular apparatus.

Downstream of the interaction chambers there is a rupture disc (27), which bursts at 1 MPa (150 psi) in the event of a build up of pressure caused by a blockage in the apparatus pipework.

Suspension leaves the interaction chamber via outlet (29). The outlet may be connected to a conduit for returning suspension that has not yet reached the desired particle size to the recycling tank (not shown) ready for another pass through the Microfluidizer®). The machine operates comfortably at up to 1.6 liters per minute (depending on the particular combination of interaction chamber(s) employed) at an operating pressure of typically 34 MPa (5,000 psi). A typical batch is 12 liters, and is generally passed up to 50 times through the apparatus.

When the mass median diameter of particles in the suspension has reached the desired particle size, the suspension may be fed from outlet (29) into the recycling tank before being diluted, mixed with other excipients and transferred to a means for sterile packaging (not shown), for example into sterile ampoules.

FIG. 5 shows a cross-section of the left hand side of the intensifier part (100) of the modified apparatus. The following description of the left-hand side of the intensifier applies also to the right-hand side, since the intensifier is symmetrical.

The intensifier comprises two main sections—plunger barrel (110) and isolation chamber (145). A plunger (115) is housed in the plunger barrel (110) and is connected via cam nut (135) to a connecting rod (140), which is located in the isolation chamber (145). The cam nut (135) is screwed tightly onto the end of connecting rod (140) but plunger (115) is held loosely in position by cam nut (135).

Cam nut (135) interacts with an air switch [not shown but located in the position surrounded by dotted lines (137)], which controls direction of movement of plunger (115) within plunger barrel (110). As plunger (115) is driven inwards within the plunger barrel, cam nut (135) approaches and then hits and triggers the air switch, changing the direction of flow of oil from the oil lines to the plunger around connecting rod (140) and forcing the plunger back in the reverse direction. The oil pressure used can be up to 34 MPa (5,000 psi), resulting in up to 210 MPa (30,000 ps)i of pressure inside the plunger barrel. In the methods of the present invention, the pressure inside the plunger barrel is generally selected to be approximately 34 MPa (5,000 psi), but may be from 6.9-69 MPa (1,000-10,000 psi).

The plunger barrel is isolated from the isolation chamber via a plunger seal located in seal location (120). The plunger seal prevents flow of suspension from the plunger barrel to the isolation chamber in use and is designed to withstand high pressures (up to 210 MPa [30,000 psi]).

Between the plunger seal and the cam nut (135) is a bushing (130) supported within bushing housing (125). The bushing supports the plunger (115) as it reciprocates within the plunger barrel.

The back of the isolation chamber (145) is provided with two oppositely facing seals (150 and 155). Seal (155) retains oil used to drive the connecting rod, whilst if there is any leakage of this oil the second seal (150) ensures it passes into drain (160). The main purpose of seal (150), however, is to prevent suspension from interfering with the hydraulic pump section of the apparatus in the event of failure of the plunger seal. Seal (150) is a lip-type seal, made from PTFE, and is capable of withstanding pressures of 1 MPa (150 psi) at 200° C. while the plunger is moving.

EXAMPLES

Example 1

Sterilising a Particle-Size Reduction Apparatus

Protocol

The sterilisation protocol of the invention has been developed for a known particle size reduction apparatus, namely a Microfluidics standard MF-210C Microfluidizer®), as part of a manufacturing process to provide sterile Budesonide suspensions for Blow-Fill-Seal production of nebulisation suspensions. The protocol is nevertheless believed to be of application to suspensions of other drugs and also to particle-size reduction using other equipment.

As an initial step, we demonstrated the ability to inactivate high levels of contamination of an isolated intensifier and check valves, and the following protocol was then developed for sterilisation of the whole apparatus, to ensure that sterilising temperatures can be achieved throughout the product contact areas and in the isolation chambers of the intensifier.

The protocol is designed to provide the temperatures and exposure times required to achieve a minimum of 121° C. for 15 minutes, using either saturated steam, or superheated water under pressure, or both, and to provide a $10^6$ reduction in *G. stearothermophilus* ATCC 7953 spores when inoculated onto components of the Microfluidizer®) considered likely to represent the most difficult challenge to sterilisation. The protocol is designed to arrive at a set of operating conditions for sterilisation in place using moist heat, employing either saturated steam or superheated water under pressure or both, which maintains at least 121° C. at internal monitoring sites. The protocol may be modified and developed in future to determine an adjusted minimum sterilising condition, including a minimum sterilising time which in future sterilisation methods may be increased to allow a margin of error in those methods.

This protocol covers the procedures to be followed during the sterilisation process. The apparatus is provided with a number of pressure transducers, and Resistance Temperature Detectors (RTDs) fitted for routine monitoring and during these studies the outputs of the RTDs and pressure transducers are fed to the validator (a Kaye Validator). Additional study thermocouples are positioned internally throughout the apparatus, wherever access is possible. Additional study thermocouples may be positioned externally to help indicate potential sites for routine monitoring.

The equipment and materials used are Microfluidizer®) Apparatus and Services, a Kaye Validator 2000, a Kaye Calibration Temperature source HTR400 or LTR140 or CTR40, or alternative equivalent provided by the applicant and a Kaye IRTD calibration reference thermometer.

All critical operating instruments used in the sterilising procedures covered by this protocol are calibrated, using standards traceable to national standards. All critical test instruments used in the protocol are calibrated according to written procedures, using standards traceable to national standards.

During the sterilisation process covered by this protocol, observations of routine temperature and pressure indicators are made, and may be modified prior to or during the studies to reflect the number of study temperature and pressure test positions built into the apparatus for these studies. Validation thermocouple data are automatically logged at a minimum frequency of every ten seconds from when heat is introduced into the test apparatus.

Test temperature sensors and the data recorder are calibrated at 100° C. and 130° C., after the test thermocouples have stabilized to under 0.2° C. per minute for 5 minutes, with the reference thermometer stabilized to within 0.012° C. during the final minute. Readings of each sensor and reference thermometer are taken at one-minute intervals for five minutes at each temperature point. Calibration of test sensors and data recorder is confirmed at 122° C. before and after qualification.

Temperatures derived from sensors and data recorder should not vary from reference temperatures by more than ±0.5° C. Only thermocouples meeting these criteria are used in the qualification.

A series of studies is conducted employing saturated steam or superheated water under pressure, to provide sterilising conditions throughout the product circuit and in the isolation chambers. The pipework is adjusted to provide suitable services for the heat source employed.

The studies are conducted over a range of temperatures and times (and, if necessary, pressures for the superheated water), until a suitable set of conditions is achieved which complies with the acceptance criteria. At least three consecutive acceptable studies are performed with unchanged sterilising settings before those settings can be considered the minimum suitable for further validation study.

Up to nine of the routine RTD temperature sensors supplied with the equipment and additional study thermocouples to a total of 36 sensors, including pressure transducers, are positioned in and on the apparatus. Internal thermocouples are introduced via appropriate Triclover®) seals. External thermocouples may if desired be held in direct contact with the stainless steel surfaces.

Data collection commences when heat is applied to the product contact circuit, and the isolation chamber, data being collected simultaneously from each temperature sensor, and each pressure sensor.

The time at which the first temperature probe reaches a minimum of 121° C., and at which all temperature probes reach 121° C. is recorded. The timed holding period commences when all test thermocouples have reached 121° C., and continues until all test thermocouples have remained above 121° C. continuously for a minimum of 15 minutes. At the end of the holding period, the apparatus is cooled. For steam sterilisations, the equipment is pressurised with air, and the steam pressure terminated. For superheated water sterilisations, the water in the circuit is cooled.

Results obtained from the above analyses must show compliance with the following criteria for any set of sterilising conditions to be considered to provide minimum conditions for further study:

(1) All internal temperature test positions must record a minimum of 121° C. continuously for at least the final 15 minutes of the holding period.

(2) For steam sterilisation, pressures measured must agree with the saturated vapour pressure of steam at the temperature measured at the same point, within ±1° C.

Results 18 steam sterilisation protocols were carried out according to the protocol described above. The first run was a control (no spores) and in the remaining 17 runs the following components of an M-210EH Microfluidizer® were inoculated with 2×10⁶ heat resistant spores of *Geobacillus stearothermophilus* ATCC No. 7953:

| | |
|---|---|
| Runs 2-4 | check valve spring retainer, intensifier plunger seal, plunger contact sealing edge. |
| Runs 5-7 | intensifier plunger seal, outer wall, behind barrel contact sealing edge. |
| Runs 8-10 | intensifier plunger seal, spring contact surface. |
| Runs 11-13 | plunger bushing inner surface |
| Runs 14-16 | plunger bushing outer surface, plastic seal support ring, surface in contact with metal seal support ring. |
| Run 17 | plunger bushing outer surface, plastic seal support ring, surface in contact with metal seal support ring, PTFE sealed-spring plunger seal. |
| Run 18 | plunger bushing inner surface, plastic seal support ring, surface in contact with metal seal support ring, Ultra High Density PE sealed-spring plunger seal. |

The steam sterilisation protocols were run to achieve 121° C. for 15 minutes (as measured using a temperature probe embedded in one intensifier barrel, close to the position of the plunger seal).

After this time, each inoculated component was then tested for sterility according to Example 4 below. All components showed a 6-log reduction in heat-resistant spores—i.e. all components passed the sterility test (MCA guidelines).

Example 2

Validating Sterility of a Seal

A seal, which has previously been contaminated with at least 1×10⁶ heat-resistant bacterial spores, is inserted into the bore of a particle-size reduction apparatus. The particle-size reduction apparatus is sterilised as described in Example 1 above and then the seal is removed from the apparatus. To validate the sterility of the apparatus bore, the seal is incubated with growth medium. A seal removed from an apparatus that has not undergone a sterilisation procedure is used as a control. The growth medium is examined for growth of microorganisms, which would indicate that the test seal (and hence the bore) had not been sterilised effectively. If there is no growth in the medium comprising the test seal, (growth being observed in the medium comprising the seal from the unsterilised bore) this indicates that sterility is achieved.

Example 3

Reduction of Particle Size of a Sterile Suspension

The mass median diameter of particles of a Budesonide suspension is reduced using an M-210EH Microfluidizer® apparatus containing, a first interaction chamber having a single circular flow passage of approximately 400 μm diameter and a second interaction chamber having a single circular flow passage of approximately 300 μm; that has previously been sterilised according to Example 1 above.

A sterile Budesonide suspension (12 liters), having particles of mass median diameter approximately 50 μm is introduced into the sterile apparatus from the reaction feed tank. The pressure used is approximately 34 MPa (5,000 psi) and the apparatus is run at 0.75 liters per minute. The suspension is passed through the apparatus and particle size is monitored during each pass. After about 30 passes the mass median diameter of particles in the suspension is reduced to 2-3 μm. The suspension is then transferred to a sterile packaging line for packaging into sterile nebules.

Example 4

Particle-Size Distribution

The use of various different interaction chambers for comminution was evaluated.

The protocol of Example 3 was repeated, however, the sterile Budesonide suspension (12 liters) was passed through a sterilised M-210EH Microfluidizer® apparatus, which had been modified to contain various different combinations of interaction chambers; i.e. interaction chambers provided with circular flow passages of diameter 200 μm, 250 μm, 300 μm or 400 μm; with or without a first interaction chamber containing a circular flow passage of 400 μm diameter.

In each batch of suspension processed, after each comminution cycle/pass the particle size of the suspension was monitored using an on-line Focused Beam Reflectance Measurement (FBRM) probe, and a sample of suspension was taken for laser diffraction analysis.

The results from the laser diffraction studies are shown in Tables 1 and 2, below. Table 1 demonstrates the particle size distribution (PSD) for the final suspension of particles compared to the target particle size distribution profile. The target size distribution profile was then changed to reflect a suspension of smaller particles and the comminution procedure was carried out using more combinations of interaction chambers.

In each comminution procedure the number of cycles/passes through the Microfluidizer® was increased or reduced until a PSD profile similar to that of the target was achieved.

TABLE 1

Results of laser diffraction analysis with selected target PSD profile

| | Flow passage diameter (μm) | | | | | | |
|---|---|---|---|---|---|---|---|
| Batch No. | 1st interaction chamber | 2nd interaction chamber | D10[1] (μm) | D50[2] (μm) | D90[3] (μm) | VMD[4] (μm) | No. of cycles |
| Target 1 | | | 1-1.25 | 4.5-6.0 | 9.0-11.0 | 3.5-5.0 | |
| 1 | 400 | 250 | 0.88 | 3.23 | 9.80 | 4.49 | 16 |
| 2 | 400 | 250 | 0.74 | 2.06 | 6.28 | 2.87 | 22 |
| 3 | 400 | 200 | 0.90 | 3.54 | 10.54 | 4.76 | 24 |

[1]10% of particles are of size given or smaller
[2]50% of particles are of size given or smaller
[3]90% of particles are of size given or smaller
[4]Volume median diameter

TABLE 2

Results of laser diffraction analysis with selected target PSD profile

| Batch No. | Flow passage diameter (μm) | | D10[1] (μm) | D50[2] (μm) | D90[3] (μm) | VMD[4] (μm) | No. of cycles |
|---|---|---|---|---|---|---|---|
| | 1st interaction chamber | 2nd interaction chamber | | | | | |
| Target 2 | | | 0.79 | 2.48 | 6.98 | 3.29 | |
| 4 | 400 | 200 | 0.73 | 2.06 | 6.28 | 2.87 | 30 |
| 5 | 400 | 200 | 0.79 | 2.48 | 6.98 | 3.29 | 31 |
| 6 | 400 | 300 | 0.68 | 1.77 | 4.88 | 2.45 | 35 |
| 7 | 400 | 300 | 0.71 | 2.01 | 6.35 | 2.85 | 30 |
| 8 | 300 | — | 0.76 | 2.27 | 6.46 | 3.02 | 20 |
| 9 | 300 | — | 0.83 | 2.52 | 6.65 | 3.21 | 17 |
| 10 | 300 | — | 0.78 | 2.29 | 6.44 | 3.02 | 19 |
| 11 | 300 | — | 0.81 | 2.34 | 6.20 | 2.99 | 16 |
| 12 | 300 | — | 0.80 | 2.30 | 6.17 | 2.97 | 16 |
| 13 | 300 | — | 0.78 | 2.17 | 5.82 | 2.81 | 16 |

[1] 10% of particles are of size given or smaller
[2] 50% of particles are of size given or smaller
[3] 90% of particles are of size given or smaller
[4] Volume median diameter

The invention claimed is:

1. An ampoule containing a sterile suspension drug comprising budesonide prepared by a method comprising:
   (a) subjecting a suspension of drug particles to a comminution procedure carried out in a sterilized particle-size reduction apparatus;
   said particle size reduction apparatus comprising at least one interaction chamber for reducing the particle size of the suspension, each interaction chamber being provided with a flow passage through which the suspension is forced, and an intensifier for forcing the suspension through the flow passage of the interaction chamber or interaction chambers,
   (b) recovering a suspension of drug particles of reduced size, wherein the mass median diameter of drug particles in the recovered suspension of drug particles is in the range between 2 to about 3 μm;
   wherein the transverse cross-sectional area of said flow passage is in the range between about $3.1 \times 10^4$ to about $2.8 \times 10^5$ μm$^2$, and
   (c) packaging the suspension into sterile ampoules.

2. The ampoule of claim 1, wherein the traverse cross-sectional area of the flow passage is in the range between about $4.9 \times 10^4$ to about $2.0 \times 10^5$ μm$^2$.

3. The ampoule of claim 2, wherein the transverse cross-sectional area of the flow passage is in the range between about $7.1 \times 10^4$ to about $1.3 \times 10^5$ μm$^2$.

4. The ampoule of claim 1, wherein the suspension is forced from the intensifier at a pressure not exceeding about 69 MPa.

5. The ampoule of claim 4, wherein the suspension is forced from the intensifier at a pressure in the range between about 21 to about 48 MPa.

6. The ampoule of claim 5, wherein the suspension is forced from the intensifier at a pressure in the range between about 28 to about 41 MPa.

7. The ampoule of claim 6, wherein the suspension is forced from the intensifier at a pressure of about 34 MPa.

8. The ampoule of claim 1, comprising a comminuted suspension of particles, produced by a method which comprises:
   (a) subjecting a suspension of drug particles to a comminution procedure carried out in a sterilised particle-size reduction apparatus;
   said particle-size reduction apparatus comprising at least one interaction chamber for reducing the particle size of the suspension, each interaction chamber being provided with a flow passage through which the suspension is forced, and an intensifier for forcing the suspension through the flow passage of the interaction chamber or interaction chambers;
   wherein the transverse cross-sectional area of said flow passage is in the range between about $3.1 \times 10^4$ μm$^2$ to about $2.8 \times 10^5$ μm$^2$;
   (b) optionally recovering a comminuted suspension of drug particles from (a);
   (c) subjecting a comminuted suspension of drug particles from (a) to at least one further comminution procedure carried out in a sterilised particle-size reduction apparatus as defined in (a);
   (d) recovering a comminuted suspension of drug particles of reduced size, wherein the mass median diameter of drug particles in the recovered suspension of drug particles is in the range between 2 to about 3 μm; and
   (e) packaging the suspension into sterile ampoules.

9. The ampoule of claim 8, wherein up to 50 comminution procedures are carried out.

10. The ampoule of claim 9, wherein from 10 to 50 comminution procedures are carried out.

11. The ampoule of claim 10, wherein from 14 to 40 comminution procedures are carried out.

12. The ampoule of claim 11, wherein from 20 to 30 comminution procedures are carried out.

13. The ampoule of claim 8, wherein (c) further comprises: recovering a comminuted suspension of drug particles after one or more further comminution procedures, measuring the size of recovered drug particles, and on the basis of the measured sizes, subjecting the suspension to one or more further comminution procedures.

14. The ampoule of claim 1 wherein the mass median diameter of drug particles in the recovered suspension of drug particles is about 3 μm.

15. The ampoule of claim 8 wherein the mass median diameter of drug particles in the recovered suspension of drug particles is about 3 μm.

* * * * *